United States Patent [19]
Tsunoda et al.

[11] Patent Number: 5,968,342
[45] Date of Patent: Oct. 19, 1999

[54] ZEOLITE CATALYST AND METHOD OF CONVERTING HYDROCARBONS USING THE SAME

[75] Inventors: Takashi Tsunoda; Mitsuhiro Sekiguchi; Tokitaka Kaneshima, all of Kurashiki, Japan

[73] Assignee: Asahi Kasei Kogyo Kabushiki Kaisha, Osaka, Japan

[21] Appl. No.: 08/809,830

[22] PCT Filed: Oct. 5, 1995

[86] PCT No.: PCT/JP95/02040

§ 371 Date: Mar. 21, 1997

§ 102(e) Date: Mar. 21, 1997

[87] PCT Pub. No.: WO96/13331

PCT Pub. Date: May 9, 1996

[30] Foreign Application Priority Data

Oct. 28, 1994 [JP] Japan ................................. 6-264996

[51] Int. Cl.$^6$ .............................. C10G 11/05; B01J 29/40
[52] U.S. Cl. ..................... 208/120.15; 208/113; 502/64; 502/60; 502/71; 502/77
[58] Field of Search ................................ 502/77, 71, 64, 502/60; 208/113, 120, 120.15

[56] References Cited

U.S. PATENT DOCUMENTS

| | | | |
|---|---|---|---|
| 3,702,886 | 11/1972 | Argauer et al. | 423/705 |
| 3,890,218 | 6/1975 | Morrison | 502/77 |
| 4,276,438 | 6/1981 | Chu | 585/467 |
| 4,608,355 | 8/1986 | Chu | 502/68 |
| 5,103,066 | 4/1992 | Dessau | 568/406 |
| 5,292,976 | 3/1994 | Dessau et al. | 585/322 |
| 5,312,995 | 5/1994 | Faraj | 568/427 |
| 5,316,661 | 5/1994 | Dessau et al. | 208/46 |

OTHER PUBLICATIONS

An Introduction to Zeolite Molecular Sieves, A. Dyer, John Wiley & Sons, New York, p. 121, 1988, no month avail.

Nicolaides et al., Applied Catalysis, 68 (1991) 31–39, Elsevier Science Publishers B.V., Amsterdam, no month avail.

Chu et al., ACS Symposium Series, Intrazeolite Chemistry, vol. 218, American Chemical Society, Washington, DC, 1983, no month avail.

*Primary Examiner*—Walter D. Griffin
*Attorney, Agent, or Firm*—Birch, Stewart, Kolasch and Birch, L.L.P.

[57] ABSTRACT

The present invention provides a catalyst to convert hydrocarbons, which comprises a zeolite containing substantially no proton and having an intermediate pore diameter, a molar ratio of $SiO_2$ to $Al_2O_3$ of at least 20 and one or more metals belonging to Group Ib of the Periodic Table. Further, the present invention provides a method to catalytically convert hydrocarbons by using the above catalyst. By means of the present invention, there can be provided a stable catalyst for conversion of hydrocarbons, which is capable of obtaining olefins containing ethylene as a main component and monocyclic aromatic hydrocarbons with good balance and a high yield, and which is hardly deteriorated by steam having a high temperature.

13 Claims, No Drawings

ZEOLITE CATALYST AND METHOD OF CONVERTING HYDROCARBONS USING THE SAME

TECHNICAL FIELD

The present invention relates to a catalyst to catalytically convert hydrocarbons and a method for catalytically converting hydrocarbons. More particularly, the present invention relates to a catalyst which catalytically crack hydrocarbon materials and a method for efficiently and stably producing lower olefins containing ethylene, which is valuable as a raw material for petrochemistry, as a main component and monocyclic aromatic hydrocarbons containing benzene, toluene and xylene as main components.

BACKGROUND ART

Heretofore, it is known to convert various hydrocarbon materials by contacting them with a solid acid catalyst, particularly an acid type (proton type) zeolite, whose alkali is removed by acid or an ammonium salt, and initiating cracking, isomerization, disproportionation, aromatization or the like reaction.

As a representative example, conversion of gas oil, heavy oil or the like into a gasoline fraction is widely conducted in petroleum refining. Further, there is proposed a method for converting light hydrocarbons into aromatic compounds by using a proton type ZSM-5 zeolite in Japanese Patent Unexamined Publication No. 41322/1974 (corresponding to British Patent No. 1381427), Japanese Patent Unexamined Publication No. 49233/1975 (corresponding to British Patent No. 1394979), Japanese Patent Unexamined Publication No. 4029/1975 (corresponding to British Patent No. 1442850) and the like. There is proposed a method for converting light hydrocarbons into lower olefins and aromatic hydrocarbons by using a proton type ZSM-5 zeolite in Japanese Patent Unexamined Publication No. 222428/1985 and Japanese Patent Unexamined Publication No. 130236/1991 and the like. There is proposed a method for converting light hydrocarbons into lower olefins by using a acid type zeolite containing silver in U.S. Pat. No. 4,361,502 and Japanese Patent Unexamined Publication No. 184638/1990.

There is proposed a method for producing aromatic hydrocarbons from light hydrocarbons in a catalyst bed having specific temperature distributions by using a specific zeolite type catalyst in International Patent Application No. PCT/JP95/01059.

As a method for obtaining lower olefins and monocyclic aromatic hydrocarbons from hydrocarbon materials, heretofore, a pyrolysis method is widely used. However, the method needs severe reaction conditions because of use of pyrolysis so that a lot of methane, which is difficult to use as a raw material for petrochemistry, is produced as a by-product. Further, the method has problems that since the ratio of product yield of olefins such as ethylene, propylene and the like and monocyclic aromatic hydrocarbon such as benzene, toluene and the like is substantially fixed, product flexibility is poor because of its yield structure, and the total yield of olefins and cyclic aromatic hydrocarbons (effective product yield) does not exceed about 60% by weight.

Therefore, in order to solve these problems of the pyrolysis method, heretofore, a method for catalytically cracking hydrocarbons by using a solid acid catalyst, particularly an acid type (proton type) zeolite catalyst has been studied. However, none of the known methods is satisfactory as a method for efficiently and stably obtaining both lower olefins (olefins having 2 to 4 carbon atoms, that is, ethylene, propylene and butene) containing ethylene, which is useful as a raw material for petrochemistry, as a main component and cyclic aromatic hydrocarbons (aromatic hydrocarbon having 6 to 9 carbon atoms, which contain benzene and alkylbenzene), and obtaining a yield of lower olefins containing ethylene as a main component higher than that of cyclic aromatic hydrocarbons.

For example, a catalytic conversion method using Y type zeolite produces a lot of paraffins, which are low value, and in addition produces extremely little aromatic hydrocarbons. A method using a proton type ZSM-5 zeolite generally provides a relatively high yield of hydrocarbons, a cracking gas composition having mainly light paraffins such as ethane, propane and the like, and poor selectivity of lower olefins. In order to improve selectivity of lower olefins, a method for introducing copper or silver is known (Japanese Patent Unexamined Publication Nos. 1413/1990 and 184638/1990). However, the method improves the yield of propylene, but provides low yields of ethylene and aromatic hydrocarbons.

Further, in the above method for catalytically cracking hydrocarbons by using the acid type zeolite, since coke is accumulated on the catalyst, a regeneration operation is often necessary to remove the coke by burning it off. The above method has a problem that the catalyst is permanently deactivated because of the repeated regeneration operation. This phenomenon occurs because the zeolite is hydrolyzed by steam, which is generated by burning of coke, and aluminum is released from the zeolite crystal so that proton active sites disappear. When the proton type zeolite is used in this kind of a reaction, this phenomenon is an unavoidably big problem. In order to solve this problem, there is proposed a method for inhibiting the above decrease of activity by introducing silver into the proton type zeolite (Japanese Patent Unexamined Publication No. 117584/1984 and U.S. Pat. No. 4,845,063). However, this method has problems such that the effect of the inhibition is not sufficient and besides, with respect to yield, the selectivity of lower olefins is low. Further, in order to inhibit accumulation of coke, there is proposed a method for contacting a zeolite with steam under specific temperature distributions in International Patent Unexamined Publication No. WO95/09050.

The present invention provides a stable catalyst for conversion of hydrocarbons, which is capable of obtaining olefins containing ethylene as a main component and monocyclic aromatic hydrocarbons with good balance and a high yield, and which is scarcely deteriorated by steam having a high temperature. Further, the present invention provides a production method by using the above method.

DISCLOSURE OF THE INVENTION

The present inventors have made extensive and intensive studies concerning a method for efficiently obtaining lower olefins and cyclic aromatic hydrocarbons from raw materials containing one type or more hydrocarbons, and obtaining a yield of lower olefins containing ethylene as a main component higher than that of cyclic aromatic hydrocarbons in order to solve the above problems. As a result, they have found that when a catalyst which comprises a zeolite containing substantially no protons and having an intermediate pore diameter and a Group lb metal is used, surprisingly, lower olefins and cyclic aromatic hydrocarbons are efficiently and stably obtained, and further, lower olefins containing ethylene as a main component are obtained with a higher yield than monocyclic aromatic hydrocarbons.

That is, the present invention provides a catalyst to convert hydrocarbons, which comprises a zeolite containing substantially no protons and having an intermediate pore diameter, a molar ratio of $SiO_2$ to $Al_2O_3$ of at least 20 and one or more metals belonging to Group Ib of the Periodic Table.

The present invention will be described in more detail below.

A zeolite having an intermediate pore diameter in the present invention has a pore diameter between that of a zeolite including A type zeolite as a representative small diameter example and that of a zeolite including mordenite, X type zeolite and Y type zeolite as representative large diameter examples. The zeolite having an intermediate pore diameter has an effective pore diameter of about 5 to about 6.5 Å. Representative examples of the zeolites having an intermediate pore diameter include ZSM-5, ZSM-8, ZSM-11, ZSM-12, ZSM-21, ZSM-23, ZSM-35 and ZSM-38. ZSM-5 group of zeolites such as ZSM-5, ZSM-11 and ZSM-8, and ZSM-38 are preferred. ZSM-5 is particularly preferred. Further, there can be used a zeolite similar to ZSM-5 and ZSM-11 described in P. A. Jacobs and J. A. Martens, "Stud. Surf. Sci. Catal." 33,PP. 167–215 (1987, Holland).

Further, it is necessary that the zeolite of the present invention has a molar ratio of $SiO_2$ to $Al_2O_3$ of at least 20 in view of stability of the catalyst. The maximum of the molar ratio of $SiO_2$ to $Al_2O_3$, is not particularly limited. However, generally, a zeolite having a molar ratio of $SiO_2$ to $Al_2O_3$, of 20 to 500, preferably 28 to 300 is used.

In the catalyst of the present invention, it is necessary that the zeolite having an intermediate pore diameter contains substantially no protons. "Substantially no proton" mentioned here means that the amount of protons measured by ion exchange in a liquid phase-titration by the filtered liquid method is 0.02 millimole/1 g of the zeolite or less, preferably 0.01 millimole/1 g of the zeolite or less. The ion exchange in a liquid phase-titration by the filtered liquid method is described in Intraszeolite Chemistry, "ACS Symp. Ser.", 218, pp. 369–382 (1983, America), Nippon Kagaku Kaishi [3], pp. 521–527 (1989) and the like.

The ion exchange in a liquid phase-titration by the filtered liquid method mentioned in the present invention is a method which comprises calcining a zeolite in air at a temperature of 400 to 600° C., conducting ion exchange of 1.5 g of the calcined zeolite in 25 ml of a 3.4 mole/l NaCl solution under ice cooling for 10 min., filtering the solution, washing the zeolite with 50 ml of pure water, recovering the total amount of a filtered liquid, and measuring the amount of protons of the zeolite from the neutralization point by titrating the filtered liquid to neutralize it with a 0.1 N NaOH aqueous solution. It is known that an ammonium ion type zeolite and a multivalent metal cation type zeolite such as a rare earth metal ion type zeolite generate protons by heat treatment. Therefore, when the amount of protons is measured, it is necessary to use a sample subjected to the above burning treatment and conduct measurement.

One preferred embodiment of the zeolite containing substantially no protons of the present invention is an alkali metal ion and/or alkali earth metal ion type zeolite. An alkali metal ion type is preferred. Na and/or K ion type zeolite having an intermediate pore diameter is particularly preferred. A zeolite having an intermediate pore diameter, which comprises both Na and/or K ion and an alkali earth metal ion, can be preferably used.

The method for producing an alkali metal ion and/or alkali earth metal ion type zeolite having an intermediate pore diameter is not particularly limited. A known ion exchange method may be used. Anyway, in order to substantially remove an acid site of a zeolite, it is important to sufficiently conduct ion exchange with an alkali metal ion and/or an alkali earth metal ion.

Another preferred embodiment of the zeolite containing substantially no protons of the present invention is a zeolite subjected to heat treatment, preferably heat treatment in the presence of steam, or a zeolite subjected to pretreatment by repeating reaction-regeneration and the like. Heat treatment is conducted, preferably at a temperature of 500° C. or more, more preferably at a temperature of 500 to 900° C. Steam treatment is conducted in conditions of preferably a temperature of 500° C. or more, more preferably a temperature of 500 to 900° C., and a steam partial pressure of 0.01 atmospheric pressure. The above treatment may be conducted before introducing one or more metals belonging to Group Ib of the Periodic Table. However, the above treatment is preferably conducted after the introduction of the metal.

In the present invention, it is necessary to introduce one or more metals belonging to Group Ib of the Periodic Table to the above zeolite. Among metals belonging to Group Ib of the Periodic Table, copper and silver are preferred. Silver is particularly preferred. Methods for introducing one or more metals belonging to Group Ib of the Periodic Table include an ion exchange method, which is conventionally conducted, an impregnation method and a kneading method. The ion exchange method is particularly preferred. An introduced Group Ib metal may exist in a form of an oxide. However, at least part of it must exist as a cation in a zeolite. Metal salts to be used include silver nitrate, silver acetate, silver sulfate, copper chloride, copper sulfate and gold chloride. The content of Group Ib metal based on the zeolite is preferably 0.1 to 10% by weight, more preferably 0.2 to 5% by weight. If the content of the Group Ib metal is less than 0.1% by weight, activity is not sufficient. Even if more than 10% by weight is added, the performance of the catalyst is not further improved.

The order or time to introduce an alkali metal ion and/or alkali earth metal ion, and the Group Ib metal is not particularly limited. After the zeolite is changed to the alkali metal ion and/or alkali earth metal ion type, the Group Ib metal may be introduced. Conversely, after the Group Ib metal is introduced, the zeolite may be changed to the alkali metal ion and/or alkali earth metal ion type. In either case, it is important to prepare the zeolite so that the prepared zeolite may contain substantially no acid sites.

If necessary, these zeolites can be used after calcining. The calcining temperature is generally 500° C. to 900° C.

Further, in order to impart an appropriate particle form in use, a porous material of refractory inorganic oxides such as alumina, silica, silica-alumina, zirconia, titania, diatomaceous earth and clay can be incorporated into a zeolite as a matrix or a binder, and molded.

Raw materials containing one or more hydrocarbons in the present invention include a normal paraffin having about 2 to about 25 carbon atoms, an isoparaffin having about 2 to about 25 carbon atoms, an olefin having about 2 to about 25 carbon atoms, a cycloparaffin having about 4 to about 25 carbon atoms and a cycloparaffin having about 4 to about 25 carbon atoms and an alkyl group of a side chain, as a main component. For example, there are gases such as ethane, propane, butane and butene; pentane, pentene, hexane, heptane, octane and a light naphtha containing them as main components; a heavy naphtha; a straight-run naphtha; coal and gas oil fraction mainly containing $C_{10}$ to $c_{20}$; and gas oil fraction obtained under a reduced pressure, which contains $C_{19}$ to $c_{25}$. Particularly, propane, butane, butene, pentane, pentene, a mixture of them and a naphtha fraction are preferred.

In the present invention, the above catalyst is used in a catalytic cracking reaction, that is, lower olefins and monocyclic aromatic hydrocarbon can be produced by contacting the above hydrocarbon materials with the catalyst for conversion of hydrocarbons at a high temperature.

The conditions for the catalytic cracking reaction in the present invention depend on the hydrocarbon materials. However, a temperature of 550 to 750° C. and a partial pressure of hydrocarbons of 0.1 to 10 atmospheric pressure are preferred. More preferably, a temperature of 570 to 700° C. and a partial pressure of hydrocarbons of 0.2 to 8 atmospheric pressure are used.

It is necessary to control the contact time of hydrocarbon materials with the catalyst by taking the pyrolysis properties of hydrocarbon materials and the reaction temperature into consideration so that effect of pyrolysis may not become excessive. However, generally, 1 second or less is appropriate.

In the catalytic cracking reaction of the present invention, any reaction style, for example, a fixed-bed type, a moving-bed type, a fluidized-bed type and an air flow carrier type, is acceptable. However, reaction styles of a fluid catalytic cracking (FCC) type, in which a catalyst can be continuously regenerated, and a quick contact (QC) type can be preferably used. QC type reaction style is described in "QC-A New Reaction System", 1989 Inter-national Fluidization Conference, Fluidization VI Proceedings, Banff, Canada, May 7–12.

In the catalytic cracking reaction, regeneration of the catalyst is conducted by generally burning coke on the catalyst to remove it in inert gas containing air or oxygen at a temperature of 400 to 900° C. When a FCC type reaction apparatus is used, a regeneration temperature higher than the reaction temperature is necessary to provide reaction heat. However, the catalyst of the present invention is hardly deteriorated and stable in regeneration having such a high temperature because the catalyst of the present invention has high water heat stability.

Further, the catalyst of the present invention can be used in a catalytic cyclization reaction by adding a metal component for hydrogenation or dehydrogenation. Particularly, when at least one metal selected from metals belonging Group IIb, Group IIIb and Group VIII of the Periodic Table and compounds of them is added, dehydrogenation and cyclization performance of the zeolite is improved. Therefore, an appropriate catalyst can be obtained to produce a monocyclic aromatic hydrocarbon from a light hydrocarbon. metals belonging to Group IIb, Group IIIb and Group VIII of the Periodic Table and compounds of them are preferably zinc, gallium, indium, nickel, palladium, platinum, an oxide of them and a composite oxide of them, more preferably zinc, zinc oxide and a composite oxide of zinc such as zinc aluminate. The amount of metals belonging to Group IIb, Group IIIb and Group VIII of the Periodic Table and compounds of them based on the zeolite is preferably 0.1 to 20% by weight.

Conditions of the catalytic cyclization reaction in the present invention depend on the hydrocarbon materials, particularly the amount ratio of olefins and paraffins. However, a temperature of 300 to 650° C., a partial pressure of hydrocarbons of 1 to 30 atmospheric pressure and a weight hour space velocity (WHSV) of 0.1 to 50 $hr^{-1}$ are preferred. A temperature of 400 to 600° C. is more preferred.

In the catalytic cyclization reaction of the present invention, any reactor of a fixed-bed type, a moving-bed type and a fluidized-bed type can be used. The reaction style is not particularly limited. However, a preferable reactor is a fixed-bed, adiabatic reactor having a simple structure.

In the catalytic cyclization reaction, regeneration of the catalyst is conducted by generally burning coke on the catalyst to remove it in inert gas containing air or oxygen at a temperature of 400 to 700° C.

BEST MODE FOR CARRYING OUT THE INVENTION

Hereinafter, the present invention will be described in more detail with reference to examples and the like.

EXAMPLE 1

A ZSM-5 type zeolite ($SiO_2/Al_2O_3$=126) was prepared by filtering, washing with water, drying and calcining in air at 550° C. after hydrothermal synthesis. A $Na^+$ type ZSM-5 was prepared by subjecting the ZSM-5 type zeolite to ion exchange in a 3.4 N sodium chloride aqueous solution (10 ml/g-zeolite) at 90° C. for 3 hours, filtering, washing with water and drying at 110° C. Next, catalyst 1 was prepared by subjecting the $Na^+$ type ZSM-5 to ion exchange at room temperature for 3 hours by a 0.02 N silver nitrate aqueous solution (10 ml/g-zeolite), filtering, washing with water, drying and calcining in air at 550° C. The amount of acid in the catalyst measured by ion exchange in a liquid phase-titration by the filtered liquid method was 0.004 mmol/g. From the result of analysis, the composition represented by a molar ratio of an oxide based on an anhydride is as follows:

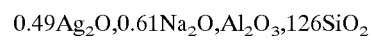

Performance to convert hydrocarbons was examined by using Catalyst 1. 2 g of the sifted catalyst having a particle size of 8 to 16 mesh was charged into a quartz reaction tube (inside diameter: 16 mmØ). The temperature was raised to a determined temperature under atmospheric pressure while nitrogen was passed at 100 cc/min. Next, a raw material naphtha (specific gravity: 0.684, composition: 79% by weight of paraffins, 15% by weight of naphthenes, 5.9% by weight of aromatic hydrocarbons, 0.1% by weight of olefins) was fed into the reaction tube at 31.3 cc/hr. The composition was analyzed by directly introducing a reaction product obtained 6 min. from the beginning of naphtha feed into a gas chromatograph. The result of reaction at 680° C. was shown Table 1.

COMPARATIVE EXAMPLE 1

Conversion reaction of the naphtha was conducted under the same conditions as in Example 1 except that $Na^+$ type ZSM-5 (Comparative Catalyst 1) obtained in Example 1 was used without further treatment. The amount of acid in the catalyst was 0.006 mmol/g. The result is shown in Table 1.

COMPARATIVE EXAMPLE 2

A $H^+$ type ZSM-5 was prepared by subjecting the ZSM-5 type zeolite ($SiO_2/Al_2O_3$=126) used in Example 1 to ion exchange in a 1 N nitric acid aqueous solution (10 ml/g-zeolite) at room temperature for 3 hours, filtering, washing with water and drying at 110° C. Next, a $H^+$ type ZSM-5 containing silver (Comparative Catalyst 2) was prepared by subjecting the $H^+$ type ZSM-5 to ion exchange at room temperature for 3 hours by a 0.1 N silver nitrate aqueous solution (10 ml/g-zeolite), filtering, washing with water, drying and calcining in air at 550° C. The amount of acid in the catalyst was 0.055 mmol/g. From the result of analysis, the composition represented by a molar ratio of a oxide based on an anhydride is as follows:

0.48Ag$_2$O,Al$_2$O$_3$,126SiO$_2$

Conversion reaction of the naphtha by using Comparative Catalyst 2 was conducted under the same conditions as in Example 1. The result is shown in Table 1.

COMPARATIVE EXAMPLE 3

Following the procedure of Example 1, pyrolysis of the naphtha was conducted at 680° C. except that porcelain Raschig rings (outside diameter: 3 mmØ, length: 3 mm) were charged instead of the zeolite. The result is shown in Table 1.

EXAMPLE 2

A Na$^+$ type ZSM-5 containing copper was prepared as in Example 1 except that a 0.1 N copper chloride aqueous solution was used instead of the 0.02 N silver nitrate aqueous solution. The amount of acid in the catalyst was 0.006 mmol/g. From the result of analysis, the composition represented by a molar ratio of a oxide based on an anhydride is as follows:

0.50Cu$_2$O,0.40Na$_2$O,Al$_2$O$_3$,126SiO$_2$

Conversion reaction of the naphtha using the catalyst was conducted under the same conditions as in Example 1. The result is shown in Table 1.

In Table 1, it is found that the Na$^+$ type ZSM-5 exhibits little cracking activity of the naphtha and cracking activity is extremely improved by introducing silver or copper into the Na$^+$ type ZSM-5. Further, selectivity of lower olefins containing ethylene as a main component is extremely improved in yield composition obtained by using AgNa$^+$ type ZSM-5, which is extremely different from that obtained by using AgH$^+$ type ZSM-5 obtained by introducing silver into acid type ZSM-5.

EXAMPLE 3

A Na$^+$ type ZSM-5 containing silver (Catalyst 2) was prepared by the procedure of Example 1 except that a concentration of the silver nitrate aqueous solution was changed to 0.1 N. The amount in acid of the catalyst was 0.004 mmol/g. From the result of analysis, the composition represented by a molar ratio of a oxide based on an anhydride is as follows:

0.88Ag$_2$O,0.15Na$_2$,Al$_2$O$_3$,126SiO$_2$

Conversion reaction of the naphtha by using Catalyst 2 was conducted under the same conditions as in Example 1 except that the reaction temperature was changed to 660° C. The result is shown in Table 2.

EXAMPLE 4

Using the procedure of Example 3, Conversion reaction of the naphtha was conducted except that the reaction temperature was changed to 680° C. The result is shown in Table 2.

EXAMPLE 5

K$^+$ type ZSM-5 containing silver (Catalyst 3) was prepared as in Example 1 except that sodium chloride was changed to potassium chloride and the concentration of the silver nitrate aqueous solution was changed to 0.1 N. The amount of acid in the catalyst was 0.002 Mmol/g. From the result of analysis, the composition represented by a molar ratio of an oxide based on an anhydride is as follows:

0.60Ag$_2$O,0.44K$_2$O,Al$_2$O$_3$,126SiO$_2$

Conversion reaction of the naphtha using Catalyst 3 was conducted under the same conditions as in Example 1 except that the reaction temperature was changed to 660° C. The result is shown in Table 2.

EXAMPLE 6

Conversion reaction of the naphtha was conducted under the same conditions as in Example 5 except that the amount of charged catalyst was change from 2 g to 3 g and the reaction temperature was changed to 680° C. The result is shown in Table 2.

COMPARATIVE EXAMPLE 4

Pyrolysis of the naphtha was conducted under the same conditions as in Comparative Example 3 except that the reaction temperature was changed to 790° C. The result is shown in Table 2.

As shown in Table 2, according to the method of the present invention, yields of methane and heavy fractions, which are low value, are lower than those of the pyrolysis technique, effective yield (the total yield of ethylene, propylene and C$_{6-8}$ aromatic hydrocarbons) can be extremely higher than that using pyrolysis and selectivity is excellent.

EXAMPLE 7

Catalyst 4 was prepared by subjecting Na$^+$ type ZSM-5 (SiO$_2$/Al$_2$O$_3$=91) to ion exchange at room temperature for 3 hours by a 0.05 N silver nitrate aqueous solution (10 ml/g-zeolite), filtering, washing with water, drying and burning in air at 550° C. The amount of acid of the catalyst was 0.002 mmol/g. From the result of analysis, the composition represented by a molar ratio of a oxide based on an anhydride is as follows:

0.61Ag$_2$O,0.26Na$_2$O,Al$_2$O$_3$,91SiO$_2$ 2 g of Catalyst 4 was charged into the quartz reaction tube used in Example 1. The temperature was raised to a predetermined temperature under atmospheric pressure while nitrogen was passed at 100 cc/min. Passing of nitrogen was stopped to conduct a reaction in the condition of no dilution and then the same raw material of naphtha as used in Example 1 was fed into the reaction tube at 46.8 cc/hr. The reaction product obtained 6 min. from the beginning of naphtha feed was analyzed. The result is shown in Table 3.

EXAMPLE 8

Catalyst 5 was prepared by subjecting a Na$^+$ type ZSM-5 (SiO$_2$/Al$_2$O$_3$=30) to ion exchange at room temperature for 3 hours by a 0.03 N silver nitrate aqueous solution (10 ml/g-zeolite), washing with water, drying and calcining in air at 550° C. The amount of acid in the catalyst was 0.002 mmol/g. From the result of analysis, the composition represented by a molar ratio of a oxide based on an anhydride is as follows:

0.24Ag$_2$O,0.79Na$_2$O,Al$_2$O$_3$,30SiO$_2$

Conversion reaction of the naphtha by using Catalyst 5 was conducted under the same conditions as in Example 1. The result is shown in Table 3.

COMPARATIVE EXAMPLE 5

An experiment was conducted under the same conditions as in Example 7 except that the H$^+$ type ZSM-5 zeolite from Comparative Example 2 was used and the amount of the catalyst was 1 g. The result is shown in Table 3.

COMPARATIVE EXAMPLE 6

A $H^+$ type ZSM-5 was prepared by subjecting the $Na^+$ ZSM-5 type zeolite used in Example 8 to ion exchange at room temperature for 3 hr. by using a 1 N nitric acid aqueous solution (10 ml/g-zeolite). Next, Comparative Catalyst 3 was prepared by conducting ion exchange in a 0.03 N silver nitrate aqueous solution (10 ml/g-zeolite) at room temperature for 3 hr. The amount of acid in the catalyst was 0.42 mmol/g. In the result of analysis, the composition represented by a molar ratio of a oxide based on an anhydride is as follows:

$0.16Ag_2O,Al_2O_3,30SiO_2$

Conversion reaction of the naphtha by using Comparative Catalyst 3 was conducted under the same conditions as in Example 1 except that the amount of the charged catalyst was changed to 1 g. The Result is shown in Table 3.

EXAMPLE 9

A $Mg^{2+}Na^+$ type ZSM-5 was prepared by subjecting a $Na^+$ type ZSM-5 zeolite ($SiO_2/Al_2O_3$=91) to ion exchange in a 1 N magnesium nitrate aqueous solution (10 ml/g-zeolite) at 90° C. for 2 hr., filtering, washing with water and drying at 110° C. Next, a $Mg^{2+}Na^+$ type ZSM-5 containing silver (Catalyst 6) was prepared by subjecting the $Mg^{2+}Na^+$ type ZSM-5 to ion exchange at room temperature for 3 hr. using a 0.1 N silver nitrate aqueous solution (10 ml/g-zeolite), filtering, washing with water, drying and calcining in air at 550° C. The amount of acid in the catalyst was 0.002 mnol/g. From the result of analysis, the composition represented by a molar ratio of a oxide based on an anhydride is as follows:

$0.58Ag_2O,0.36MgO,0.08Na_2O,Al_2O_3,91SiO_2$

Conversion reaction of the naphtha using Catalyst 6 was conducted under the same conditions as in Example 1 except that the reaction product obtained 4 min. from the beginning of naphtha feed was analyzed. The Result is shown in Table 4.

EXAMPLE 10

A $Ca^{2+}Na^+$ type ZSM-5 containing silver was prepared as in Example 9 except that magnesium nitrate was changed to calcium nitrate. The amount of acid in the catalyst was 0.003 mmol/g. From the result of analysis, the composition represented by a molar ratio of a oxide based on an anhydride is as follows:

$0.60Ag_2O,0.32CaO,0.08Na_2O,Al_2O_3,91SiO_2$

Conversion reaction of the naphtha using the catalyst was conducted under the same conditions as in Example 9. The Result is shown in Table 4.

EXAMPLE 11

A $Ba^{2+}Na^+$ type ZSM-5 containing silver was prepared as in Example 9 except that magnesium nitrate was changed to barium nitrate. The amount of acid in the catalyst was 0.002 mmol/g. From the result of analysis, the composition represented by a molar ratio of a oxide based on an anhydride is as follows:

$0.46Ag_2O,0.60BaO,0.04Na_2O,Al_2O_3,91SiO_2$

Conversion reaction of the naphtha using the catalyst was conducted under the same conditions as in Example 9. The Result is shown in Table 4.

EXAMPLE 12

A $Ba^{2+}Na^+$ type ZSM-5 containing silver was prepared as in Example 11 except that ZSM-5 type zeolite ($SiO_2/Al_2O_3$=91) was changed to ZSM-5 type zeolite ($SiO_2/Al_2O_3$=175). The amount of acid in the catalyst was 0.002 mmol/g. From the result of analysis, the composition represented by a molar ratio of a oxide based on an anhydride is as follows:

$0.78Ag_2O,0.02BaO,0.20Na_2O,Al_2O_3,175SiO_2$

Conversion reaction of the naphtha using the catalyst was conducted under the same conditions as in Example 1. The Result is shown in Table 4.

EXAMPLE 13

A catalyst containing 0.3% by weight of silver was prepared by subjecting a $H^+$ ZSM-5 type zeolite ($SiO_2/Al_2O_3$=175) to ion exchange in a 0.006 N nitric acid aqueous solution (10 ml/g-zeolite) at room temperature for 3 hr., washing with water, drying and calcining in air at 550° C. Next, nitrogen was passed at a flow rate of 485 cc/min. under atmospheric pressure and the temperature of the catalyst layer was controlled at 750° C. Steaming treatment was conducted under the conditions of a temperature of 750° C. and a steam partial pressure of 0.4 atm. for 40 min. by running pure water at a flow rate of 15.6 cc/min for 40 min. After steam treatment, the amount of acid in the catalyst was 0.018 mmol/g.

Conversion reaction of the naphtha using the catalyst was conducted under the same conditions as in Example 1. The Result was shown in Table 5.

EXAMPLE 14

A catalyst containing 1.3% of silver by weight was prepared as in Example 13 except that a concentration of the silver nitrate was changed to 0.1 N. Steaming treatment was conducted under the same conditions as in Example 13. After steaming treatment, the amount of acid of the catalyst was 0.013 mmol/g.

Conversion reaction of the naphtha using the catalyst was conducted under the same conditions as in Example 1. The result is shown in Table 5.

COMPARATIVE EXAMPLE 7

Conversion reaction of the naphtha using the zeolite used in Example 13 but, which was not subjected to the steam treatment described in Example 13 was conducted under the same conditions as in Example 1. The Result is shown in Table 5. The amount of acid in the catalyst was 0.118 mmol/g.

COMPARATIVE EXAMPLE 8

Conversion reaction of the naphtha using the zeolite described in Example 14,but which was not subjected to the steam treatment of Example 14 was conducted under the same conditions as in Example 1. The result is shown in Table 5. The amount of acid in the catalyst was 0.055 mmol/g.

EXAMPLE 15

The following experiments were conducted to compare resistance to catalyst deterioration caused by steam having a high temperature.

2 g of the same catalyst as Catalyst 2 prepared in Example 3 was charged into a quartz reaction tube. Nitrogen was passed at a flow rate of 485 cc/min under atmospheric pressure and the temperature of the catalyst layer was controlled at 750° C. Steaming treatment was conducted under the conditions of a temperature of 750° C. and a steam partial pressure of 0.4 atm. for 2 hr. by feeding pure water at a flow rate of 15.6 cc/min for 2 hr. Next, conversion reaction of the naphtha was conducted under the same conditions as in Example 1 in order to evaluate reaction activity of the catalyst. A linear reaction rate constant was calculated from a conversion of n-pentane contained in the naphtha according the following equation (1). The result is shown in Table 6. The calculation of contact time was conducted based on a vacant column by using average compositions of the inlet and outlet.

$$R=\theta^{-1}\times \ln\{1/(1-y)\} \quad (1)$$

R: Reaction rate constant of naphtha cracking (sec.$^{-1}$)
θ: contact time (sec.)
y; conversion of n-pentane
y=(a−b)/a
a: amount of n-pentane in naphtha (wt. %)
b: amount of n-pentane in reaction product (wt. %)

COMPARATIVE EXAMPLE 9

The same experiment as in Example 15 was conducted except that the catalyst, the charged amount and steaming treatment time were changed to H$^+$ type ZSM-5 zeolite used in Comparative Example 2, 4 g and 40 min. respectively. The result is shown in Table 6.

COMPARATIVE EXAMPLE 10

The same experiment as in Example 15 was conducted except that the catalyst was changed to Comparative Catalyst 2 used in Comparative Example 2. The result is shown in Table 6.

As shown in Table 6, when the acid type zeolite used in Comparative Example 8 was contacted with steam having a high temperature, activity was extremely lowered in a short time. To the contrary, activity of the catalyst of the present invention was only sligthly lowered and was stable. Further, the catalyst of the present invention was extremely improved in resistance to deterioration, compared with the acid type zeolite containing silver (Comparative Catalyst 2).

EXAMPLE 16

A Na$^+$ type ZSM-5 zeolite catalyst containing silver (Catalyst 7) was prepared as in Example 7 except that the concentration of the silver nitrate was changed to 0.1 N. The amount of acid in the catalyst was 0.002 mmol/g. From the result of analysis, the composition represented by a molar ratio of a oxide based on an anhydride is as follows:

0.82Ag$_2$O,0.15Na$_2$O,Al$_2$O$_3$,91SiO$_2$

Conversion reaction of the naphtha using the Catalyst 7 was conducted under the same conditions as in Example 1 for 6 min. Next, reaction gas in the reaction tube was replaced by passing 100 cc/min for 10 min. of nitrogen for 2 min. and then air was passed with 100 cc/min. Coke accumulated on the catalyst was burned off to remove it by conversion reaction of the naphtha. Further, nitrogen was passed at 100 cc/min. for 2 min. to replace air and gas produced by burning coke.

Based on 1 cycle as extending from the conversion reaction of the naphtha to second time of passing nitrogen, 264 cycles were carried out. The results from the first cycle and 264th cycle are shown in Table 7.

A linear reaction rate constant was measured by replacing the value of n-pentane with the total value of C$_5$–C$_8$, paraffin, C$_5$–C$_8$ naphtenes and C$_5$–C$_8$ olefins in equation (1).

COMPARATIVE EXAMPLE 11

238 cycles were carried out under the same conditions as in Example 16 by using H$^+$ type ZSM-5 zeolite used in Comparative Example 2 as a catalyst. The results from the 7th cycle and 238th cycle are shown in Table 7.

As shown in Table 7, according to the method of the present invention, even if the conversion reaction of the naphtha and regeneration operation were repeated, the catalyst was not deteriorated and effective product yield and selectivity can be maintained.

EXAMPLE 17

Na$^+$ type ZSM-5 zeolite (Sio$_2$/Al$_2$O$_3$=73) was subjected to ion exchange in a 0.1 N silver nitrate aqueous solution (10 ml/g-zeolite) at room temperature for 3 hr., washed with water and dried. A catalyst having a average particle diameter of 65$\mu$ and containing 50% by weight of silica was obtained by adding 10 kg of SNOWTEX N manufactured by Nissan Chemical Industries, ltd. (3 kg by weight of silica) to 3 kg of the dried catalyst and using a spray dryer.

2.5 g of the catalyst was charged into a reaction tube. Conversion reaction of the naphtha was conducted under the same conditions as in Example 7 except that sampling was conducted 4.5 min. from the beginning of naphtha feed. The result was shown in Table 8. The amount of acid in the catalyst was 0.005 mmol/g-zeolite. From the result of analysis, the composition represented by a molar ratio of a oxide based on an anhydride is as follows:

0.55Ag$_2$O,0.33Na$_2$O,Al$_2$O$_3$,150SiO$_2$

EXAMPLE 18

80 parts by weight of Na$^+$ type ZSM-5 zeolite (Sio$_2$/Al$_2$O$_3$=50) and 20 parts by weight of γ-alumina were kneaded and then pellets having a diameter of 1.6 mm and a length of 4 to 6 mm were molded by conducting extrusion molding. Next, a molded ZSM-5 zeolite catalyst was obtained by drying at 120° C. for 4 hr. and calcining at 500° C. for 3 hr. The catalyst was subjected to ion exchange in a 0.1 N silver nitrate aqueous solution (10 ml/g-zeolite) at room temperature 3 hr., washed with water and dried. At this time, the amount of acid in the catalyst was 0.005 mmol/g-zeolite. A molded ZSM-5 zeolite catalyst containing zinc (Catalyst 8) was obtained by impregnation in a 3 N silver nitrate aqueous solution (0.5 ml/g-zeolite) and calcining. From the result of analysis, the composition represented by a molar ratio of a oxide based on an anhydride is as follows:

5.1ZnO,0.40Ag$_2$O,0.34Na$_2$O,8.9Al$_2$O$_3$,50SiO$_2$ 100 g of Catalyst 8 was charged into a reaction tube made of stainless steel having a diameter of 1 inch. The temperature of the catalyst layer was raised to 650° C. under a pressure of 5 Kg/cm$^2$ G. Steaming treatment was conducted under the conditions of a steam partial pressure of 0.8 atm. for 5 hr. After steaming treatment, a hydrocarbon material (propane: 0.1 wt. %, propylene: 0.2 wt. %, butane: 7.7 wt. %, butene: 32.0 wt. %, pentane: 45.7 wt. %, pentene: 14.3 wt. %) was fed into the reaction tube at 280 g/hr., and then conversion reaction of the hydrocarbon was conducted. The reaction results obtained at 4 hr. and 40 hr. from beginning of the material feed are shown in Table 9.

COMPARATIVE EXAMPLE 12

60 parts by weight of $H^+$ type ZSM-5 zeolite ($SiO_2$/$Al_2O_3$=50), 15 parts by weight of γ-alumina and 25 parts of zinc nitrate were kneaded and then pellets having a diameter of 1.6 mm and a length of 4 to 6 mm were molded by conducting extrusion molding. Next, the molded $H^+$ type ZSM-5 zeolite catalyst containing of zinc (Comparative Catalyst 4) was obtained by drying at 120° C. for 4 hours and calcining at 500° C. for 3 hours. The amount of acid in the $H^+$ type ZSM-5 zeolite was 0.24 mmol/g. From the result of analysis, the composition represented by a molar ratio of a oxide based on an anhydride is as follows:

5.2ZnO,8.6$Al_2O_3$,50$SiO_2$

Steaming treatment and conversion reaction of the hydrocarbon were conducted under the same conditions as in Example 18 using Comparative Catalyst 4. The result is shown Table 9.

As shown in Table 9, according to the method of the present invention, high selectivity can be maintained.

EXAMPLE 19

4 g of Catalyst 8 was charged into the quartz reaction tube used in Example 1. Nitrogen was passed at a flow rate of 143 cc/min. under atmospheric pressure and the temperature of the catalyst layer was controlled at 650° C. Steaming treatment was conducted under the conditions of a temperature of 650° C. and a steam partial pressure of 0.8 atm. for 5 hr. by feeding pure water at a flow rate of 27.6 cc/min for 5 hr. After steaming treatment, the temperature was raised to a determined temperature and passing of nitrogen was stopped. A raw material of n-hexane was fed into the reaction tube at 23.4 cc/hr. The composition of a reaction product obtained at 30 min. from the beginning of n-hexane feed was analyzed by directly introducing the reaction product into a gas chromatograph.

After coke on the catalyst was burned off by passing air with 100 cc/min., the above steaming treatment and conversion reaction of n-hexane were conducted again. The result is shown in Table 10.

COMPARATIVE EXAMPLE 13

An experiment was conducted under the same conditions as in Example 19 except that Comparative Catalyst 4 was used. The result is shown in Table 10.

As shown in Table 10, the catalyst of the present invention exhibits high activity and was little deteriorated by steam having a high temperature.

Industrial Applicability

As mentioned above, according to the present invention, there can be provided a stable catalyst for conversion of hydrocarbons, which is capable of obtaining olefins containing ethylene as a main component and monocyclic aromatic hydrocarbons with good balance and a high yield, and which is little deteriorated by steam having a high temperature. Therefore, the present invention can be widely used in the petrochemical industry and petroleum refining. Particularly, the present invention can be effectively used in production of lower olefins such as ethylene, propylene and the like, aromatic compounds and gasoline having high octane number.

TABLE 1

|  | Ex. 1 | Comp. Ex. 1 | Comp. Ex. 2 | Comp. Ex. 3 | Ex. 2 |
|---|---|---|---|---|---|
| Zeolite | AgNa type | Na type | AgH type | Pyrolysis | CuNa type |
| Amount of acid (mmol/g) | 0.004 | 0.006 | 0.055 | — | 0.006 |
| Hydrocarbon material | Naphtha | Naphtha | Naphtha | Naphtha | Naphtha |
| Reaction temperature (° C.) | 680 | 680 | 680 | 680 | 680 |
| Yield (wt. %) |  |  |  |  |  |
| Hydrogen | 1.2 | 0.2 | 4.3 | 0.1 | 1.6 |
| Methane | 9.3 | 3.2 | 8.4 | 2.6 | 8.5 |
| Ethylene | 22.8 | 6.1 | 14.6 | 5.1 | 17.8 |
| Propylene | 19.5 | 6.5 | 8.9 | 5.6 | 16.1 |
| Butene | 5.4 | 4.6 | 1.5 | 4.1 | 4.0 |
| $C_{6-8}$ aromatic hydrocarbon | 19.8 | 9.7 | 45.0 | 8.9 | 28.4 |
| $C_9^+$ hydrocarbon | 1.5 | 1.4 | 5.5 | 1.3 | 1.9 |
| $C_{6-9}$ aromatic hydrocarbon | 20.5 | 11.0 | 45.9 | 10.1 | 29.3 |
| $C_{2-4}$ olefin | 47.7 | 17.2 | 25.0 | 14.8 | 37.9 |

TABLE 2

|  | Ex. 3 | Ex. 4 | Ex. 5 | Ex. 6 | Comp. Ex. 4 |
|---|---|---|---|---|---|
| Zeolite | AgNa type | AgNa type | AgK type | AgK type | Pyrolysis |
| Amount of acid (mmol/g) | 0.004 | 0.004 | 0.002 | 0.002 | — |
| Hydrocarbon material | Naphtha | Naphtha | Naphtha | Naphtha | Naphtha |
| Reaction temperature (° C.) | 660 | 680 | 660 | 680 | 790 |
| Amount of charged catalyst (g) | 2.0 | 2.0 | 2.0 | 3.0 | — |
| Yield (wt. %) |  |  |  |  |  |

TABLE 2-continued

|  | Ex. 3 | Ex. 4 | Ex. 5 | Ex. 6 | Comp. Ex. 4 |
|---|---|---|---|---|---|
| Hydrogen | 1.5 | 1.2 | 1.2 | 1.5 | 0.8 |
| Methane | 9.5 | 9.4 | 7.4 | 9.5 | 13.5 |
| Ethylene | 22.8 | 24.1 | 21.3 | 24.9 | 24.6 |
| Propylene | 17.2 | 18.1 | 20.3 | 17.4 | 16.7 |
| Butene | 4.4 | 4.9 | 6.2 | 4.0 | 6.2 |
| $C_{6-8}$ aromatic hydrocarbon | 23.9 | 21.2 | 18.4 | 22.7 | 12.1 |
| $C_9^+$ hydrocarbon | 1.7 | 1.4 | 1.5 | 2.1 | 2.7 |
| $C_{2-3}$ olefin + $C_{6-8}$ aromatic hydrocarbon | 63.9 | 63.4 | 60.0 | 65.0 | 53.4 |

TABLE 3

|  | Ex. 7 | Ex. 8 | Comp. Ex. 5 | Comp. Ex. 6 |
|---|---|---|---|---|
| Zeolite | AgNa type | AgNa type | H type | AgH type |
| Hydrocarbon material | Naphtha | Naphtha | Naphtha | Naphtha |
| Amount of acid (mmol/g) | 0.002 | 0.002 | 0.096 | 0.42 |
| Reaction temperature (° C.) | 680 | 680 | 680 | 680 |
| Amount of charged catalyst (g) | 2.0 | 2.0 | 1.0 | 1.0 |
| Yield (wt. %) |  |  |  |  |
| Hydrogen | 1.0 | 1.3 | 1.5 | 3.1 |
| Methane | 10.3 | 11.4 | 10.3 | 11.8 |
| Ethylene | 25.2 | 20.8 | 20.1 | 12.8 |
| Propylene | 17.9 | 17.1 | 14.8 | 9.5 |
| Butene | 2.2 | 4.5 | 3.4 | 2.6 |
| $C_{6-8}$ aromatic hydrocarbon | 24.5 | 23.7 | 30.4 | 35.1 |
| $C_9^+$ hydrocarbon | 2.8 | 2.9 | 3.6 | 6.9 |
| $C_{6-9}$ aromatic hydrocarbon | 26.7 | 24.4 | 32.7 | 36.4 |
| $C_{2-4}$ olefin | 45.2 | 42.4 | 38.2 | 25.0 |

TABLE 4

|  | Ex. 9 | Ex. 10 | Ex. 11 | Ex. 12 |
|---|---|---|---|---|
| Zeolite | AgMgNa type | AgCaNa type | AgBaNa type | AgBaNa type |
| Amount of acid (mmol/g) | 0.002 | 0.003 | 0.002 | 0.002 |
| Hydrocarbon material | Naphtha | Naphtha | Naphtha | Naphtha |
| Reaction temperature (° C.) | 680 | 680 | 680 | 680 |
| Amount of charged catalyst (g) | 2.0 | 2.0 | 2.0 | 2.0 |
| Yield (wt. %) |  |  |  |  |
| Hydrogen | 1.1 | 1.2 | 1.0 | 1.3 |
| Methane | 7.0 | 7.3 | 6.9 | 8.1 |
| Ethylene | 21.9 | 22.4 | 22.1 | 21.1 |
| Propylene | 21.0 | 20.6 | 22.6 | 20.1 |
| Butene | 5.7 | 5.4 | 6.3 | 5.5 |
| $C_{6-8}$ aromatic hydrocarbon | 21.7 | 21.9 | 18.4 | 22.0 |
| $C_9^+$ hydrocarbon | 2.2 | 2.2 | 1.9 | 1.3 |
| $C_{6-9}$ aromatic hydrocarbon | 23.1 | 23.2 | 19.7 | 22.7 |
| $C_{2-4}$ olefin | 48.6 | 48.4 | 50.9 | 46.7 |

TABLE 5

|  | Ex. 13 | Ex. 14 | Comp. Ex. 7 | Comp. Ex. 8 |
|---|---|---|---|---|
| Amount of silver (wt. %) | 0.3 | 1.3 | 0.3 | 1.3 |
| Amount of acid (mmol/g) | 0.018 | 0.013 | 0.118 | 0.055 |
| Hydrocarbon material | Naphtha | Naphtha | Naphtha | Naphtha |
| Reaction temperature (° C.) | 680 | 680 | 680 | 680 |
| Yield (wt. %) |  |  |  |  |
| Hydrogen | 1.8 | 2.1 | 4.1 | 4.3 |
| Methane | 10.1 | 12.5 | 10.2 | 8.4 |
| Ethylene | 22.3 | 23.5 | 16.7 | 14.6 |
| Propylene | 18.1 | 13.3 | 8.2 | 8.9 |
| Butene | 4.5 | 2.5 | 1.0 | 1.5 |
| $C_{6-8}$ aromatic hydrocarbon | 27.4 | 32.7 | 42.9 | 45.0 |
| $C_9^+$ hydrocarbon | 1.0 | 1.3 | 5.8 | 5.5 |
| $C_{6-9}$ aromatic hydrocarbon | 27.9 | 33.2 | 43.8 | 45.9 |
| $C_{2-4}$ olefin | 44.9 | 39.3 | 25.9 | 25.0 |

TABLE 6

|  | Ex. 15 | | Comp. Ex. 9 | | Comp. Ex. 10 | |
| --- | --- | --- | --- | --- | --- | --- |
| Catalyst | AgNaZSM-5 | | HZSM-5 | | AgHZSM-5 | |
| Steaming Conditions | | | | | | |
| Temperature (° C.) | 750 | | 750 | | 750 | |
| Partial Pressure of steam | 0.4 | | 0.4 | | 0.4 | |
| Treatment time (min.) | 120 | | 40 | | 120 | |
| Reaction Conditions | Pre-treatment | Post-treatment | Pre-treatment | Post-treatment | Pre-treatment | Post-treatment |
| Amount of catalyst (g) | 2.0 | 2.0 | 2.0 | 4.0 | 2.0 | 2.0 |
| Temperature (° C.) | 685 | 677 | 682 | 672 | 683 | 692 |
| Contact time (sec.) | 0.24 | 0.24 | 0.24 | 0.49 | 0.24 | 0.24 |
| Conversion of n-pentane (%) | 97.5 | 95.5 | 98.6 | 81.2 | 96.0 | 91.9 |
| Reaction rate constant* (sec.$^{-1}$) | 14.6 | 13.2 | 17.6 | 3.7 | 13.2 | 9.1 |
| (Relative value) | (100) | (90) | (100) | (21) | (100) | (69) |

*Amended value at 680° C. (activation energy: 22 kcal/mol)

TABLE 7

|  | Ex. 16 | | Comp. Ex. 11 | |
| --- | --- | --- | --- | --- |
| Catalyst | AgNa type | | H type | |
| Amount of acid (mmol/g) | 0.002 | | 0.096 | |
| Cycle Number | 1 | 264 | 7 | 238 |
| Hydrocarbon material | Naphtha | Naphtha | Naphtha | Naphtha |
| Reaction temperature (° C.) | 679 | 685 | 674 | 687 |
| Yield (wt. %) | | | | |
| Hydrogen | 1.3 | 1.5 | 1.3 | 1.2 |
| Methane | 9.4 | 9.8 | 10.1 | 9.3 |
| Ethylene | 21.6 | 21.4 | 20.7 | 19.4 |
| Propylene | 18.3 | 18.5 | 16.2 | 20.3 |
| Butene | 4.8 | 4.9 | 4.3 | 6.4 |
| $C_{6-8}$ aromatic hydrocarbon | 26.7 | 29.3 | 28.8 | 24.5 |
| $C_9^+$ hydrocarbon | 2.3 | 1.9 | 2.2 | 1.5 |
| $C_{2-4}$ olefin + $C_{6-9}$ aromatic hydrocarbon | 66.6 | 69.2 | 65.7 | 64.2 |
| Conversion of $C_{5-8}$ PNO (%) | 94.9 | 95.9 | 94.9 | 91.0 |
| Reaction rate constant* (sec.$^{-1}$) | 12.4 | 12.5 | 13.2 | 9.2 |
| (Relative value) | (100) | (100) | (100) | (70) |

*Amended value at 680° C. (activation energy: 22 kcal/mol)
$C_{5-8}$ PNO: $C_{5-8}$ paraffin, $C_{5-8}$ naphthene, and $C_{5-8}$ olefin

TABLE 8

|  | Ex. 17 |
| --- | --- |
| Zeolite | AgNa type ZSM-5/SiO$_2$ |
| Amount of acid (mmol/g) | 0.005 |
| Hydrocarbon material | Naphtha |
| Reaction temperature (° C.) | 675 |
| Amount of charged catalyst (g) | 2.5 |
| Yield (wt. %) | |
| Hydrogen | 0.8 |
| Methane | 8.6 |
| Ethylene | 22.6 |
| Propylene | 18.2 |
| Butene | 5.2 |
| $C_{6-8}$ aromatic hydrocarbon | 23.5 |
| $C_9^+$ hydrocarbon | 2.9 |
| $C_{6-9}$ aromatic hydrocarbon | 25.1 |
| $C_{2-4}$ olefin | 46.0 |

TABLE 9

|  | Ex. 18 | | Comp. Ex. 12 | |
| --- | --- | --- | --- | --- |
| Amount of acid (mmol/g) | 0.005 | | 0.24 | |
| Reaction time (hr.) | 4 | 40 | 4 | 41 |
| Reaction temperature (° C.) | 517 | 517 | 517 | 517 |
| Reaction pressure (kg/cm$^2$G) | 5.0 | 5.0 | 5.0 | 5.0 |
| WHSV (hr.$^{-1}$) | 2.81 | 2.81 | 2.81 | 2.81 |
| Yield (wt. %) | | | | |
| Hydrogen | 1.7 | 1.5 | 1.3 | 1.4 |
| Non-aromatic hydrocarbon | 45.4 | 46.2 | 53.6 | 54.7 |
| $C_{5-8}$ aromatic hydrocarbon | 46.9 | 43.8 | 38.5 | 37.9 |
| $C_9^+$ aromatic hydrocarbon | 6.0 | 6.9 | 6.6 | 6.0 |
| Conversion of aromatic hydrocarbon (wt. %) | 52.9 | 50.7 | 45.1 | 44.0 |

TABLE 10

|  | Ex. 19 | | Comp. Ex. 13 | |
| --- | --- | --- | --- | --- |
| Amount of acid (mmol/g) | 0.005 | | 0.24 | |
| Steaming treatment time (hr.) | 5 | 10 | 5 | 10 |
| Reaction temperature (° C.) | 528 | 528 | 531 | 530 |
| Conversion of n-hexane (%) | 82.2 | 77.7 | 57.2 | 41.4 |
| Yield (wt. %) | | | | |
| $C_{6-9}$ hydrocarbon | 33.8 | 30.9 | 17.0 | 11.1 |
| Reaction rate constant (sec.$^{-1}$) | 0.86 | 0.77 | 0.40 | 0.24 |
| (Relative value) | (100) | (90) | (100) | (60) |

*Amended value at 530° C. (activation energy: 22 kcal/mol)

We claim:

1. A catalyst to convert hydrocarbons, which comprises a zeolite containing substantially no protons and having an intermediate pore diameter, a molar ratio of $SiO_2$ to $Al_2O_3$ of at least 20 and silver.

2. The catalyst to convert hydrocarbons according to claim 1, wherein the zeolite is used in an alkali metal ion form and/or an alkali earth metal ion form.

3. The catalyst to convert hydrocarbons according to claim 1, wherein the zeolite is ZSM-5.

4. The catalyst to convert hydrocarbons according to claim 2, wherein the zeolite is ZSM-5.

5. A method for producing a lower olefin and a monocyclic aromatic hydrocarbon by contacting a raw material containing one or more hydrocarbons with the catalyst according to claim 1 at a temperature of 550 to 750° C., wherein the lower olefin is obtained at a higher yield than the monocyclic aromatic hydrocarbon.

6. The catalyst to convert hydrocarbons according to the catalyst of any one of claims 1, 2, 3 or 4, further comprising at least one metal belonging to Group IIb, Group IIIb and Group VIII of the Periodic Table and compounds of them.

7. A method for producing a monocyclic aromatic hydrocarbon by contacting a raw material containing one or more hydrocarbons with the catalyst of claim 6 in the gas phase at a temperature of 650° C. or less.

8. The catalyst to convert hydrocarbons according to any one of claims 1, 2, 3 or 4, wherein the molar ratio of $SiO_2$ to $Al_2O_3$ is 20 to 500.

9. The catalyst to convert hydrocarbons according to any one of claims 1, 2, 3 or 4, wherein the content of silver metal based on the zeolite is 0.1 to 10% by weight.

10. The method for producing a lower olefin and a monocyclic aromatic hydrocarbon according to claim 5, wherein the zeolite is used in an alkali metal ion form and/or an alkali earth metal ion form.

11. The method for producing a lower olefin and a monocyclic aromatic hydrocarbon according to claim 5, wherein the zeolite is ZSM-5.

12. The method for producing a monocyclic aromatic hydrocarbon according to claim 7, wherein the zeolite is used in an alkali metal ion form and/or an alkali earth metal ion form.

13. The method for producing a monocyclic aromatic hydrocarbon according to claim 7, wherein the zeolite is ZSM-5.

* * * * *